United States Patent
Tian et al.

(10) Patent No.: US 10,602,996 B2
(45) Date of Patent: Mar. 31, 2020

(54) METHOD AND APPARATUS FOR GENERATING DENTAL PANORAMIC IMAGE, AND PANORAMIC CAMERA FOR PHOTOGRAPHING TEETH

(71) Applicant: HEFEI MEYER OPTOELECTRONIC TECHNOLOGY INC., Hefei, Anhui (CN)

(72) Inventors: Ming Tian, Anhui (CN); Maoxian Lin, Anhui (CN); Dong Jiang, Anhui (CN); Yu Niu, Anhui (CN); Guangjie Cai, Anhui (CN); Youyuan Zhao, Anhui (CN); Jianjun Zhang, Anhui (CN)

(73) Assignee: HEFEI MEYER OPTOELECTRONIC TECHNOLOGY INC., Hefei, Anhui (CN)

( * ) Notice: Subject to any disclaimer, the term of this patent is extended or adjusted under 35 U.S.C. 154(b) by 319 days.

(21) Appl. No.: 15/533,639

(22) PCT Filed: Dec. 31, 2014

(86) PCT No.: PCT/CN2014/095921
§ 371 (c)(1),
(2) Date: Jun. 6, 2017

(87) PCT Pub. No.: WO2016/090700
PCT Pub. Date: Jun. 16, 2016

(65) Prior Publication Data
US 2017/0319159 A1    Nov. 9, 2017

(30) Foreign Application Priority Data
Dec. 11, 2014   (CN) .......................... 2014 1 0764395

(51) Int. Cl.
*A61B 6/00* (2006.01)
*A61B 6/03* (2006.01)
(Continued)

(52) U.S. Cl.
CPC ................ *A61B 6/14* (2013.01); *A61B 6/032* (2013.01); *A61B 6/42* (2013.01); *A61B 6/4208* (2013.01);
(Continued)

(58) Field of Classification Search
CPC ........... A61B 6/14; A61B 6/42; A61B 6/4208; A61B 6/4233; A61B 6/44; A61B 6/4429;
(Continued)

(56) References Cited

U.S. PATENT DOCUMENTS 5,293,312 A * 3/1994 Waggener ............. G06T 11/006
378/14
5,600,699 A * 2/1997 Suzuki ..................... A61B 6/14
378/38
(Continued)

FOREIGN PATENT DOCUMENTS

CN        101079151 A       11/2007
CN        101393653 A       3/2009
(Continued)

OTHER PUBLICATIONS

Office action from SIPO for CN application 201410764395.2, dated Jan. 31, 2018.
English translation of office action from SIPO for CN application 201410764395.2, dated Jan. 31, 2018.
ISR and written opinions for PCT application CN2014095921.
(Continued)

*Primary Examiner* — Allen C. Ho
(74) *Attorney, Agent, or Firm* — Martin & Ferraro, LLP

(57) ABSTRACT

Method and apparatus for generating a dental panoramic image and panoramic camera for photographing teeth, including: determining a frame frequency of a reference detector, and determining frame frequency of a photograph-
(Continued)

ing detector; photographing teeth according to the frame frequency of the photographing detector to generate a plurality of images; performing a shift and superposition on the images to generate a first panoramic image; acquiring a fuzzy region in the first panoramic image; and performing a frame frequency adjustment on each row in the fuzzy region to generate a clear image, and fusing the clear image and the first panoramic image to generate a second panoramic image. By using different changing rules of the frame frequency for imaging for each row of the image, both cusps and roots of teeth of the patient may be arranged in a focusing layer, generating a clear image, and improving definition of the panoramic image.

19 Claims, 8 Drawing Sheets

(51) Int. Cl.
  *A61B 6/14*    (2006.01)
  *G06T 3/40*    (2006.01)
  *G06T 5/10*    (2006.01)
  *G06T 5/00*    (2006.01)
  *G06T 5/50*    (2006.01)
  *G06T 7/00*    (2017.01)
  *H04N 5/232*    (2006.01)
  *H04N 7/01*    (2006.01)

(52) U.S. Cl.
  CPC .............. *A61B 6/4233* (2013.01); *A61B 6/44* (2013.01); *A61B 6/4429* (2013.01); *A61B 6/4435* (2013.01); *A61B 6/4441* (2013.01); *A61B 6/48* (2013.01); *A61B 6/486* (2013.01); *A61B 6/50* (2013.01); *A61B 6/501* (2013.01); *A61B 6/52* (2013.01); *A61B 6/5205* (2013.01); *G06T 3/4038* (2013.01); *G06T 5/003* (2013.01); *G06T 5/10* (2013.01); *G06T 5/50* (2013.01); *G06T 7/0012* (2013.01); *H04N 5/23238* (2013.01); *H04N 7/0127* (2013.01); *G06T 2207/20201* (2013.01); *G06T 2207/20221* (2013.01); *G06T 2207/30036* (2013.01); *G06T 2207/30196* (2013.01)

(58) Field of Classification Search
  CPC ..... A61B 6/4435; A61B 6/4441; A61B 6/486; A61B 6/52; A61B 6/5205; A61B 6/032; A61B 6/48; A61B 6/50; A61B 6/501
  USPC .................. 378/19, 38–40, 196, 197, 98.8
  See application file for complete search history.

(56) References Cited

U.S. PATENT DOCUMENTS

| | | | | |
|---|---|---|---|---|
| 5,677,940 A * | 10/1997 | Suzuki | A61B 6/14 | 250/370.09 |
| 5,744,806 A * | 4/1998 | Fröjd | A61B 6/14 | 250/370.09 |
| 5,784,429 A * | 7/1998 | Arai | A61B 6/14 | 348/E5.086 |
| 5,812,191 A * | 9/1998 | Orava | G01T 1/2928 | 348/308 |
| 5,848,123 A * | 12/1998 | Strömmer | H04N 5/37206 | 378/98.8 |
| 6,055,292 A * | 4/2000 | Zeller | A61B 6/14 | 378/146 |
| 6,470,069 B1 * | 10/2002 | Müller | A61B 6/14 | 378/21 |
| 6,584,171 B2 * | 6/2003 | Suzuki | A61B 6/14 | 348/E3.023 |
| 7,016,461 B2 * | 3/2006 | Rotondo | A61B 6/14 | 378/39 |
| 7,092,483 B2 * | 8/2006 | Nyholm | A61B 6/06 | 378/38 |
| 7,136,452 B2 * | 11/2006 | Spartiotis | A61B 6/14 | 378/19 |
| 7,247,861 B2 * | 7/2007 | Suzuki | H04N 5/32 | 250/370.09 |
| 7,262,399 B2 * | 8/2007 | Hayashi | A61B 6/14 | 250/208.1 |
| 7,322,746 B2 * | 1/2008 | Beckhaus | A61B 6/032 | 378/19 |
| 7,336,763 B2 * | 2/2008 | Spartiotis | A61B 6/14 | 378/40 |
| 7,421,059 B2 * | 9/2008 | Suzuki | A61B 6/04 | 378/38 |
| 7,676,022 B2 * | 3/2010 | Pantsar | A61B 6/14 | 378/38 |
| 7,798,708 B2 * | 9/2010 | Erhardt | A61B 6/032 | 250/370.09 |
| 7,945,016 B2 * | 5/2011 | Bothorel | A61B 6/14 | 378/148 |
| 7,991,107 B2 * | 8/2011 | Sadakane | A61B 6/14 | 378/39 |
| 8,005,187 B2 * | 8/2011 | Suzuki | A61B 6/032 | 378/19 |
| 8,165,265 B2 * | 4/2012 | Niwa | G06T 11/003 | 378/27 |
| 8,279,315 B2 * | 10/2012 | De Godzinsky | H04N 3/1562 | 348/311 |
| 8,433,033 B2 * | 4/2013 | Harata | A61B 6/583 | 378/38 |
| 8,503,604 B2 * | 8/2013 | Inglese | A61B 6/14 | 378/19 |
| 8,588,364 B2 * | 11/2013 | Suzuki | A61B 6/14 | 378/38 |
| 8,634,515 B2 * | 1/2014 | Cho | A61B 6/14 | 378/27 |
| 8,662,749 B2 * | 3/2014 | Kia | G01N 23/04 | 378/189 |
| 8,736,925 B2 * | 5/2014 | Mayer | H04N 5/37213 | 235/455 |
| 8,982,262 B2 * | 3/2015 | Bugnet | H04N 5/3743 | 250/208.1 |
| 9,029,793 B2 * | 5/2015 | Spartiotis | H04N 5/32 | 250/370.09 |
| 9,036,776 B2 * | 5/2015 | Sadakane | A61B 6/145 | 378/38 |
| 9,084,568 B2 * | 7/2015 | Katsumata | A61B 6/14 | |
| 9,113,799 B2 * | 8/2015 | Katsumata | A61B 6/032 | |
| 9,148,566 B2 * | 9/2015 | Wagatsuma | A61B 6/025 | |
| 9,245,658 B2 * | 1/2016 | Desaute | A61B 6/032 | |
| 9,253,426 B2 * | 2/2016 | Mayer | H04N 5/37206 | |
| 9,384,864 B2 * | 7/2016 | Nelson | A61B 6/4216 | |
| 9,408,580 B2 * | 8/2016 | Toimela | A61B 6/14 | |
| 9,442,012 B2 * | 9/2016 | Mann | G01C 11/025 | |
| 9,888,891 B2 * | 2/2018 | Suuronen | A61B 6/4452 | |
| 10,231,681 B2 * | 3/2019 | Bruno | A61B 6/14 | |
| 10,313,566 B2 * | 6/2019 | Fereyre | H04N 5/2173 | |

FOREIGN PATENT DOCUMENTS

| | | |
|---|---|---|
| CN | 101668485 A | 3/2010 |
| CN | 102136137 A | 7/2011 |
| CN | 102469977 A | 5/2012 |
| EP | 1961383 A1 | 8/2008 |

OTHER PUBLICATIONS

English translation of the written opinions for PCT application CN2014095921.
English translation of the ISR for PCT application CN2014095921.

* cited by examiner upper teeth          lower teeth before adjustment          after adjustment

METHOD AND APPARATUS FOR GENERATING DENTAL PANORAMIC IMAGE, AND PANORAMIC CAMERA FOR PHOTOGRAPHING TEETH

CROSS-REFERENCE TO RELATED APPLICATIONS

This application is a U.S. National Phase application under 35 USC § 371 of the International Patent Application No, PCT/CN2014/095921, filed on Dec. 31, 2014; which claims priority to and benefits of Chinese Patent Application Serial No. 201410764395.2, entitled "Method and apparatus for generating dental panoramic image, and panoramic camera for photographing teeth", and filed with the State Intellectual Property Office of P. R. China on Dec. 11, 2014 by HEFEI MEIYA OPTOELECTRONIC TECHNOLOGY INC.; all of which are incorporated herein by reference.

FIELD

The present disclosure relates to a field of image processing technology, and more particularly relates to a method and an apparatus for generating a dental panoramic image and a panoramic camera for photographing teeth.

BACKGROUND

Panoramic image of oral cavity, i.e., oral pantomography, is one of significant methods for detecting oral diseases at present. It is advantageous to display images of all teeth on one X-ray film with small radiation doses.

At present, a digital panoramic image of oral cavity is usually formed by adopting a MI (Time Delay integration) sensor or a narrow area array sensor according to principles of TDI. IDE is based on several exposures of a same object. By using a delay integration method, TDI greatly increases a collection of light, thus improving a signal-noise ratio, and reducing a weight and a volume of a detector.

Working principles of TDI require a strict synchronization between a frame frequency of the detector and a movement rate of an object when scanning, and an corresponding relationship thereof is V=R*F, in which R is a pixel size (a constant), V is a relative movement rate between the object and the detector at the present moment, and F is the frame frequency of the detector at the present moment.

The problem is that, there may be situations that root imaging of incisor teeth of a patient may be unclear when the TDI sensor or the narrow area array sensor are used to form the panoramic image of oral cavity according to the principles of MI, if the patient has serious bucktooth, i.e., inclination angles of the incisor teeth are quite large, which may reduce definition of the panoramic image.

SUMMARY

Embodiments of the present disclosure seek to solve at least one of the problems existing in the related art to at least some extent.

Embodiments of a first aspect of the present disclosure provide a method for generating a dental panoramic image. The method includes: determining a frame frequency of a reference detector, and determining a frame frequency of a photographing detector according to the frame frequency of the reference detector; photographing teeth of a patient according to the frame frequency of the photographing detector to generate a plurality of images; performing a shift and superposition on the plurality of images to generate a first panoramic image; acquiring a fuzzy region in the first panoramic image; and performing a frame frequency adjustment on each row in the fuzzy region to generate a clear image, and fusing the clear image and the first panoramic image to generate a second panoramic image.

Embodiments of a second aspect of the present disclosure provide an apparatus for generating a dental panoramic image. The apparatus includes: a determining module, configured to determine a frame frequency of a reference detector, and to determine a frame frequency of a photographing detector according to the frame frequency of the reference detector; a first generating module, configured to photograph teeth of a patient according to the frame frequency of the photographing detector to generate a plurality of images; a second generating module, configured to perform a shift and superposition on the plurality of images to generate a first panoramic image; an acquiring module, configured to acquire a fuzzy region in the first panoramic image; and a third generating module, configured to perform a frame frequency adjustment on each row in the fuzzy region to generate a clear image, and to fuse the clear image and the first panoramic image to generate a second panoramic image.

Embodiments of a third aspect of the present disclosure provide a panoramic camera for photographing teeth. The panoramic camera includes the apparatus for generating a dental panoramic image according to embodiments of the second aspect of the present disclosure.

Embodiments of a fourth aspect of the present disclosure provide a storage medium for storing application programs which are configured to execute the method for generating a dental panoramic image according to embodiments of the first aspect of the present disclosure.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

Additional aspects and advantages of embodiments of present disclosure will be given in part in the following descriptions, become apparent in part from the following descriptions, or be learned from the practice of the embodiments of the present disclosure.

FIG. 2(*b*) is a schematic diagram for illustrating incisor teeth of a patient biting on an occlusion apparatus;

FIG. 4(*b*) is a flow chart of a process of a shift superposition according to an embodiment of the present disclosure;

DETAILED DESCRIPTION

Figure 1:
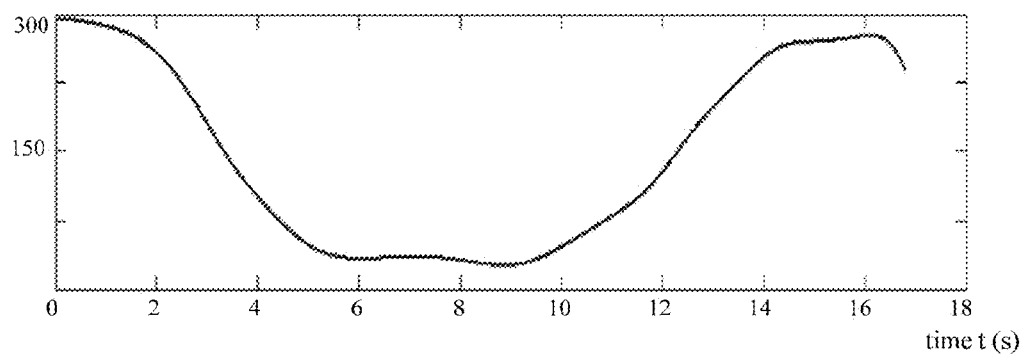
FIG. 1 is a schematic diagram for illustrating that a frame frequency used by a detector when detecting varies over time according to a fixed rule.

Reference will be made in detail to embodiments of the present disclosure, where the same or similar elements and the elements having same or similar functions are denoted by like reference numerals throughout the descriptions. The embodiments described herein with reference to drawings are explanatory, and used to generally understand the present disclosure. The embodiments shall not be construed to limit the present disclosure.

It should be understood that, in a process of capturing a panoramic image, a detector moves according to a curvilinear path. Thus, a relative velocity between dental arch of the patient and the detector is changed over time. Since the detector is fixed according to the curvilinear path in every capturing process, a rule of the relative velocity of dental arch of the patient and the detector is fixed. According to a requirement of TDI working principle, the frame frequency of the detector is strictly synchronized with a movement velocity of a target. Thus, in order to form a clear image of teeth, the frame frequency used by the detector when detecting varies over time according to a fixed rule, which is recorded as F(t) shown in FIG. 1.

Figure 2A:
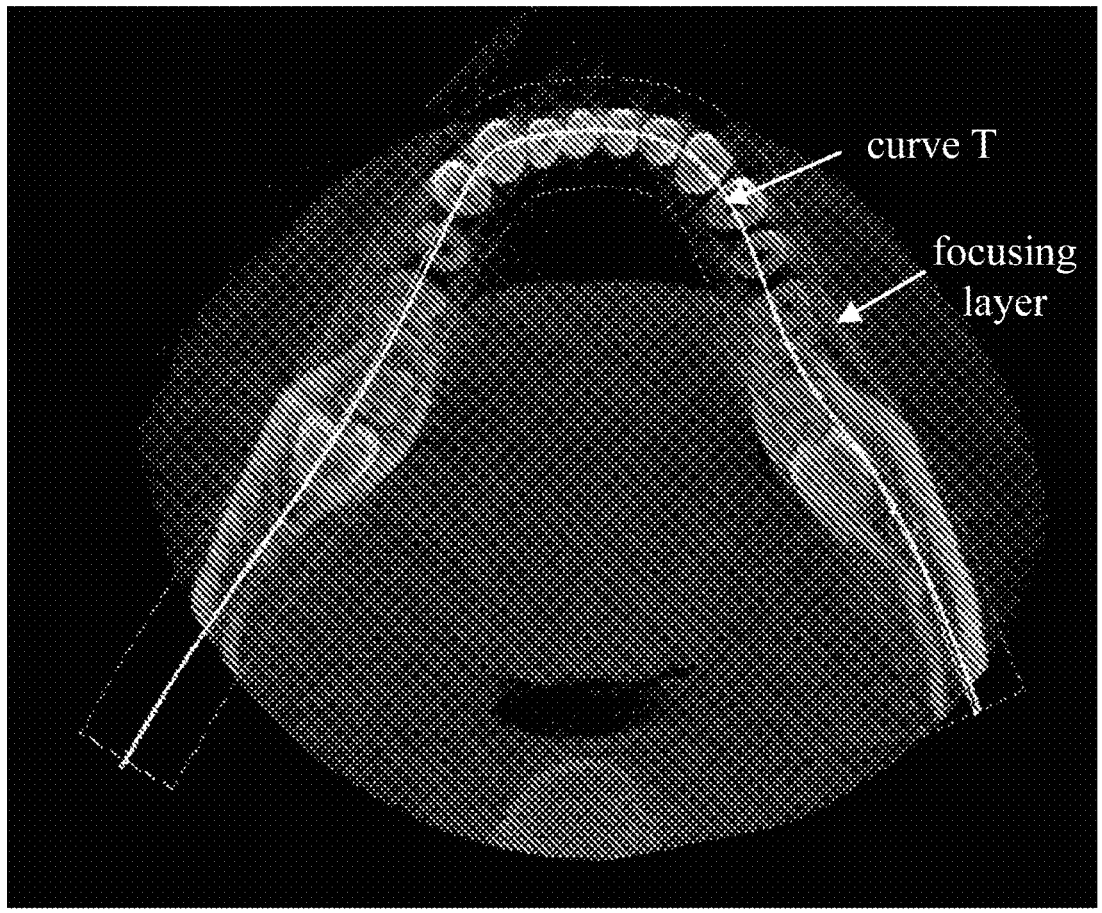
FIG. 2(*a*) is a schematic diagram of movement path of the detector for capturing teeth of a patient.
Figure 2B:
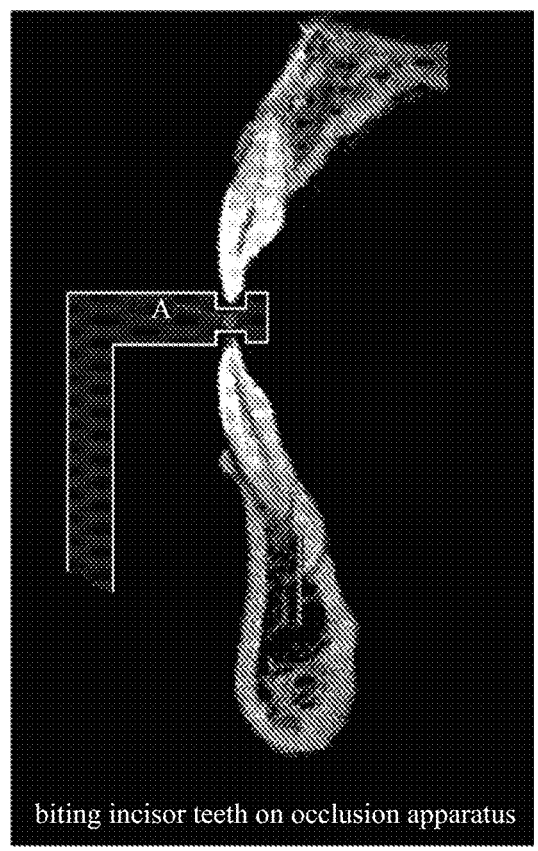

The movement path of the detector is a curve, therefore, in a case that a changing rule of the frame frequency is fixed, there is only one curve T on which the movement velocity of the object is strictly synchronized with the frame frequency of the detector in a space, as shown in FIG. 2. For convenience of description, the relative velocity between the object on this curve and the detector may refer to $V_s(t)$. In other words, the relative velocity between the object and the detector may not be strictly synchronized with the frame frequency of the detector if the object is not on the curve T. As the distance between the object and the curve T gets farther, the difference between the movement velocity and $V_s(t)$ becomes larger. When the difference is larger enough, a clear image may not be formed. It should be understood that only when the object to be photographed is located within a range close to the curve T, a clear image may be formed. Thus, the range in which the clear image may be formed can be called a focusing layer, as shown in FIG. 2(a). The changing rule F(t) of each frame frequency of the detector corresponds to a unique space curve T, and a position of the curve T (i.e., a position of the focusing layer) may be changed by changing the frame frequency, as shown in FIG. 3(c).

Figure 3:
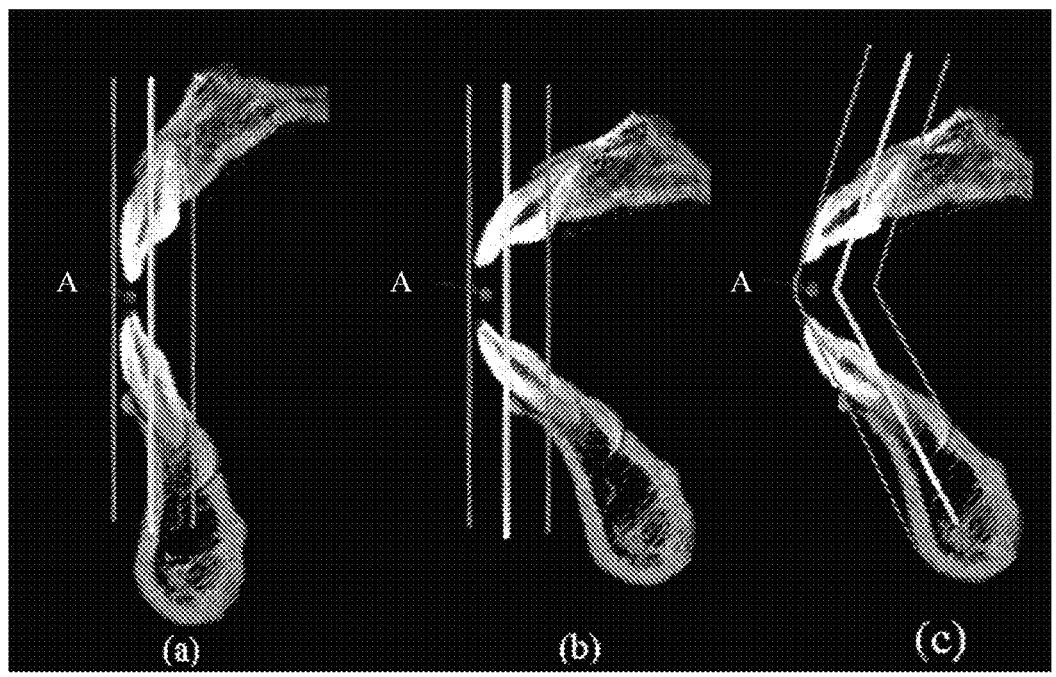
FIG. 3 shows effect diagrams for illustrating incisor teeth of different patients biting on an occlusion apparatus.

At present, the panoramic image is unclear because the teeth to be photographed are not in the focusing layer, and there are mainly two reasons for this. (1) Incisor teeth are not in the focusing layer because of a deviation of the position of the patient, which causes that the teeth can not be photographed clearly, but it can be avoided by a correct operation of a doctor. (2) There is an inclination angle of the incisor teeth generally, which is in conflict with a limited thickness of the focusing layer of the panoramic image. If the inclination angle is small, the cusps and the roots of the incisor teeth are in the focusing layer, at which time a clear image can be formed, as shown in FIG. 3(a). However, if the inclination angle is large, the cusps and the roots of the incisor teeth can not be arranged in the focusing layer at the same time, as shown in FIG. 3(b). There is an occlusion apparatus configured on a support platform of a CT (Computed Tomography) machine, which is configured to fix the position of the patient. The patient may bite the occlusion apparatus correctly when the panoramic image is captured. Since the biting position is fixed when the panoramic image is captured (point A in FIG. 3, i.e., a touch point of the teeth of the patient and the biting apparatus), the position of the patient may be fixed, in which it should be understood that the "biting apparatus" is usually made of plastic and installed on a fixed position of the machine, and the incisor teeth of the patient is required to bite on the bring apparatus whenever the panoramic image or a CT is captured.

Thus, the cusps of the incisor teeth are within the focusing layer generally, but the roots can not be covered in the focusing layer, such that the roots of the incisor teeth can not be captured clearly, in this case, traditional capturing method is unable to photograph a whole tooth clearly due to a limited thickness of the focusing layer, such that the doctor's diagnosis may be affected.

Accordingly, embodiments of the present disclosure provide a method and an apparatus for generating a dental panoramic image and a panoramic machine for photographing teeth. The main idea is that a different changing rule of the frame frequency is used to each row of the image for imaging, the frame frequency corresponding to the cusps of the incisor teeth is different from that corresponding to the roots of the incisor teeth, i.e., the changing rule of the frame frequency corresponding to the cusps $-F_{teeth\ top}(t)$ is different from that corresponding to the roots $-F_{teeth\ root}(t)$, which means that a shape of the focusing layer is changed. Thus, even though the inclination angle of the incisor teeth is large, the cusps and the roots may be covered in the focusing layer at the same time, so as to form the clear image. Specifically, the method and the apparatus for generating a dental panoramic image and the panoramic machine for photographing teeth according to embodiments of the present disclosure will be described with reference to drawings.

Figure 4:
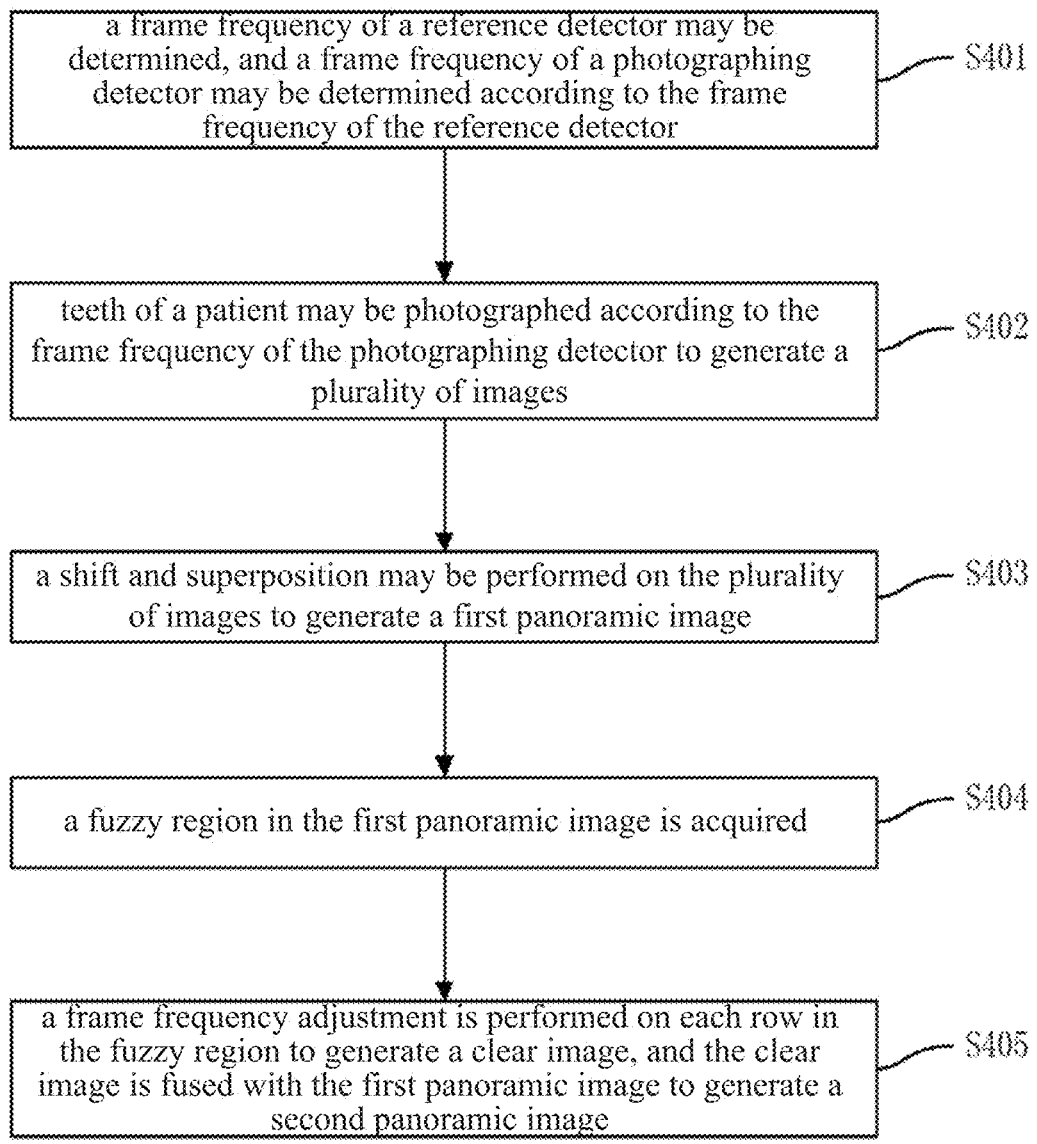
FIG. 4(*a*) is a flow chart of a method for generating a dental panoramic image according to an embodiment of the present disclosure.
Figure 4:
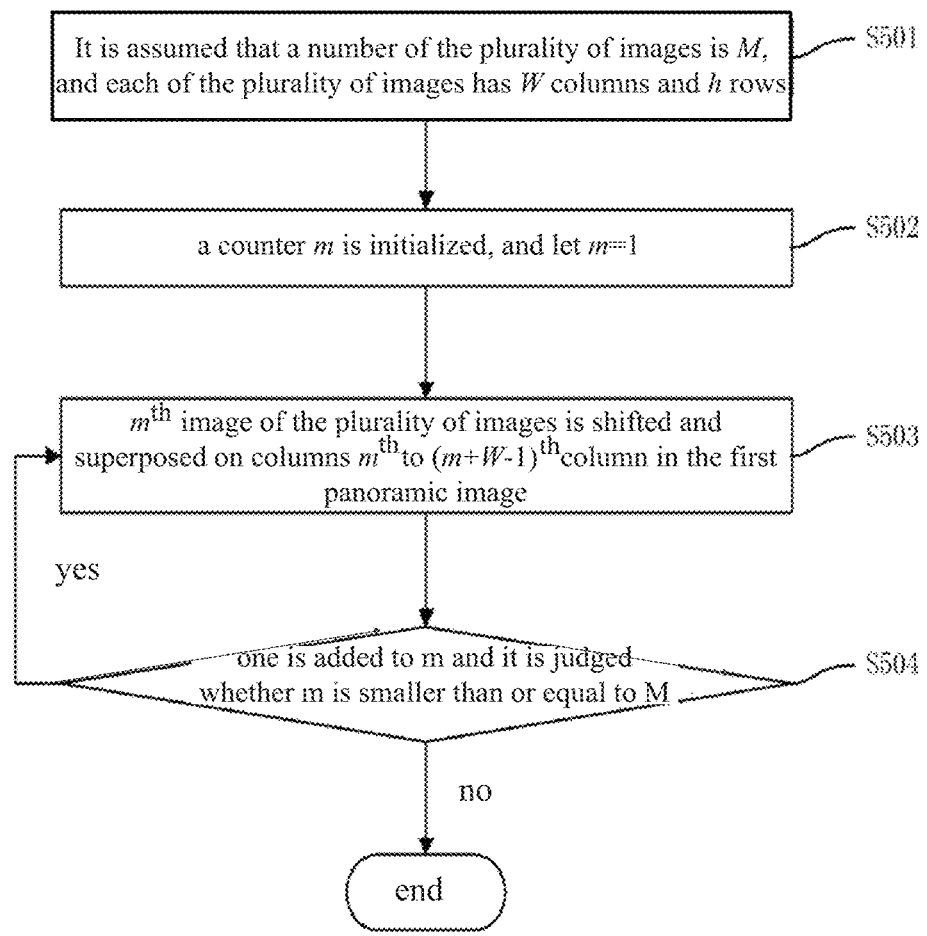

FIG. 4(a) is a flow chart of a method for generating a dental panoramic image according to an embodiment of the present disclosure. As shown in FIG. 4(a), the method may include the following acts.

In act S401, a frame frequency of a reference detector may be determined, and a frame frequency of a photographing detector may be determined according to the frame frequency of the reference detector.

Specifically, in the embodiments of the present disclosure, a process for determining the frame frequency of the reference detector may be as follows. A curve shown in FIG. 1 may be adjusted continuously to photograph until a whole image is formed clearly, at this time, the curve is defined as the frame frequency of the reference detector. The frame frequency of the photographing detector for common photographing may be determined according to the frame frequency of the reference detector after the frame frequency of the reference detector is determined.

In act S402, teeth of a patient may be photographed according to the frame frequency of the photographing detector to generate a plurality of images.

For example, the teeth of the patient may be photographed with the frame frequency of the photographing detector for common photographing by a narrow area array detector to acquire the plurality of images. It could be understood that each image corresponds to a frame, and the image corresponding to each frame may be stored as original data. It should be noted that in the embodiments of the present disclosure, the teeth of the patient may be photographed with frame frequency of the photographing detector by other kinds of detectors (such as area array detectors and the like) to generate the plurality of images.

In act S403, a shift and superposition may be performed on the plurality of images to generate a first panoramic image.

Figure 5:
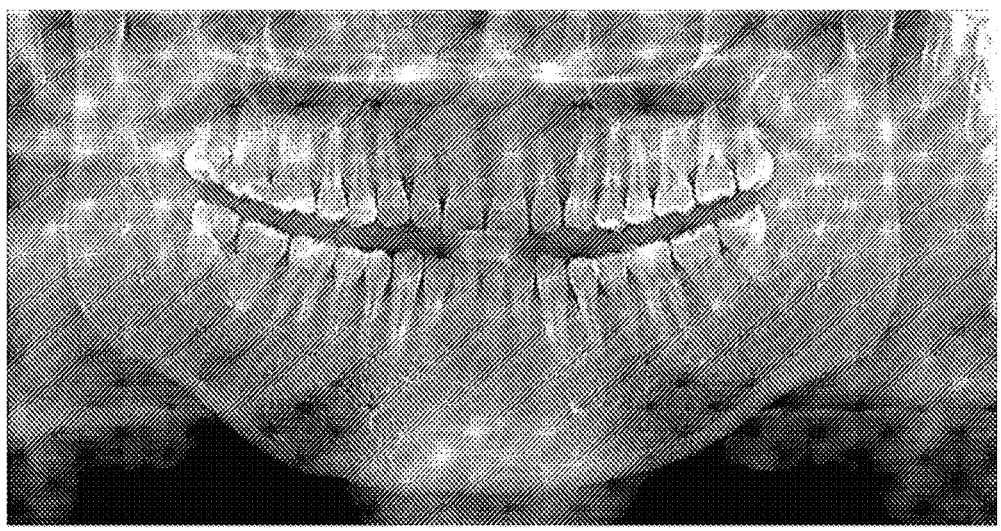
FIG. 5 is a schematic diagram of a displaying effect of a first panoramic image according to an embodiment of the present disclosure.

Specifically, the shift and the superposition may be performed on the image corresponding to each frame according to TDI principle to acquire the panoramic image (i.e., the first panoramic image). Specifically, in the embodiments of the present disclosure, as shown in FIG. 4(h), the process of the shift and the superposition is shown as follows. It is assumed that a number of the plurality of images is IV, and each of the plurality of images has W columns and h rows (S501), thus the height of the panoramic image is h rows as well. After that, a counter m is initialized, and let m=1 (S502). Then, $m^{th}$ image of the plurality of images is shifted and superposed on $m^{th}$ column to $(m+W-1)^{th}$ column in the first panoramic image (S503). After that, one is added to m, and it is judged whether m is smaller than or equal to M (S504), if m is smaller than or equal to M. S503 may be performed again until $M^{th}$ image of the plurality of images is shifted and superposed on the first panoramic image to generate the first panoramic image. In other words, all of the plurality of images are superposed on the panoramic image and a result of the superposition is an imaging result of the panoramic image (i.e., the first panoramic image). A displaying effect of the first panoramic image is shown in FIG. 5.

In act S404, a fuzzy region in the first panoramic image is acquired.

Specifically, in an embodiment of the present disclosure, the fuzzy region in the first panoramic image may be acquired by manual selection of the user, which means that the user may select the fuzzy region in the first panoramic image manually in a selection box. The fuzzy region in the first panoramic image may be acquired according to the selection of the user when it is detected that the user has selected the fuzzy region in the first panoramic image. For example, assuming that a region of the incisor teeth in the first panoramic image is not clear, the user may hold a left mouse button and drag the mouse to select the fuzzy region to be adjusted. Thus, by selecting manually, the user may select the fuzzy region which needs to be performed a sharpening processing of image according to the user's requirement.

In another embodiment of the present disclosure, the fuzzy region in the first panoramic image may be acquired automatically by judging whether each region in the first panoramic image satisfies a preset condition. A specific judging process is described as follows. It is judged whether a resolution of the first panoramic image reaches a preset threshold, if the resolution of the first panoramic image does not reach a preset threshold, a region in the first panoramic of which the resolution does not reach the preset threshold is acquired as the fuzzy region. It should be understood that the judging process is not limited to the above judging solution, other common judging solutions may be available, which will not described herein. Thus, the fuzzy region may be acquired automatically and an operation process for the user may be simplified.

In act S405, a frame frequency adjustment is performed on each row in the fuzzy region to generate a clear image, and the clear image is fused with the first panoramic image to generate a second panoramic image.

Specifically, in the embodiments of the present disclosure, firstly, a total number of rows in the fuzzy region may be acquired, and a frame frequency of the photographing detector corresponding to each row may be determined according to a preset frame frequency computation model. After that, frames in the fuzzy region are deleted according to the frame frequency of the photographing detector corresponding to each row and a preset frame extracting model to determine frames reserved for each row. Then, a TDI reorganization is performed on the fuzzy region according to the frames reserved for each row to generate the clear image, and a size of the clear image is adjusted to be same as a size of the fuzzy region which is not performed the sharpening processing of image. Finally, the adjusted clear image is fused with the first panoramic image to generate the second panoramic image. In the embodiments of the present disclosure, the preset frame frequency computation model is:

$$F_n(t)=F_0(t)*((k-1)*n+N-k)/(N-1) \tag{1}$$

wherein N is the total number of the rows in the fuzzy region, $F_n(t)$ is a frame frequency of the photographing detector of $n^{th}$ row in the fuzzy region and n=1, 2, ..., N, $F_0(t)$ is the frame frequency of the photographing detector for generating the first panoramic image, and k is a frame frequency variation amplitude and 0<k<1.

Additionally, the preset frame extracting model is:

$$l=\text{floor}(p*(F_n(t)/F_0(t)))-\text{floor}((p-1)*(F_n(t)/F_0(t))) \tag{2}$$

wherein floor( ) is an integral function for leaving a fractional part, L is a total number of the frames reserved for the fuzzy region, p=1, 2, ..., L and l<, $p^{th}$ frame is reserved for using if l is greater than or equal to 1, and $p^{th}$ frame is not reserved for using if l is smaller than 1.

Further, in the embodiments of the present disclosure, fusing the adjusted clear image and the first panoramic image to generate the second panoramic image may include following acts. A first weight of the first panoramic image and a second weight of the adjusted clear image may be determined according to a width value of a preset fusing area. After that, the second panoramic image may be generated according to a preset fusing model, the first panoramic image, the first weight, the adjusted clear image and the second weight. In the embodiments of the present disclosure, the preset fusing model is:

$$I_{new}=\text{weight1}*I_0+\text{weight2}*I_{part\_new}, \tag{3}$$

wherein $I_{new}$ is a fused image, $I_0$ is the first panoramic image, $I_{part\_new}$ is the adjusted clear image, weight1 is the first weight and weight2 is the second weight.

Figure 6:
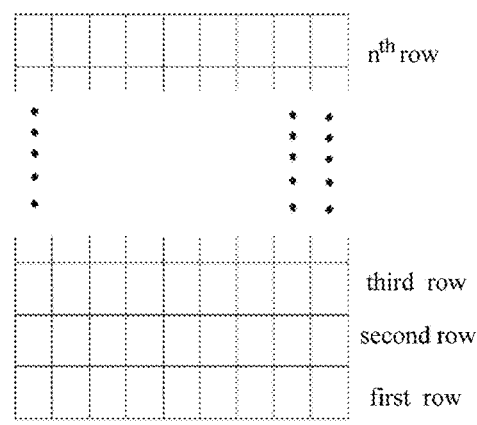
FIG. 6 illustrates schematic diagrams of arrangement of rows in narrow area array images corresponding to upper teeth and lower teeth.
Figure 6:
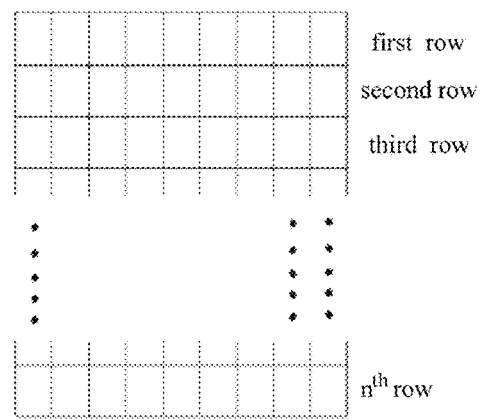

For example, if the fuzzy region is the region corresponding to the incisor teeth, a sharpening processing of image is performed on the fuzzy region (i.e., the region corresponding to the incisor teeth) firstly. The process of the sharpening processing of image will be described as follows. A frame frequency variation amplitude k (0<k<1) may be preset, and the frame frequency corresponding to each row may be determined according to the total number N of rows in the region selected, as shown in FIG. 6. The frame frequency of the photographing detector corresponding to the $n^{th}$ row is:

$$F_n(t)=F_0(t)*((k-1)*n+N-k)/(N-1)$$

After that, in terms of the $n^{th}$ row, the frame frequency corresponding to each row may be changed by extracting frames from the original data according to the newly determined frame frequency $F_n(t)$, in which extracting frames from the original data is deleting some frames in an original image sequence to reserve the frames for using. In other words, frames in the fuzzy region are deleted according to the frame frequency $F_n(t)$ of the photographing detector corresponding to each row and Equation (2) to determine the frames reserved for each row. If l in Equation (2) is greater than or equal to 1, $p^{th}$ frame is reserved for using, and if l is smaller than 1, the $p^{th}$ frame is not used.

Figure 7:
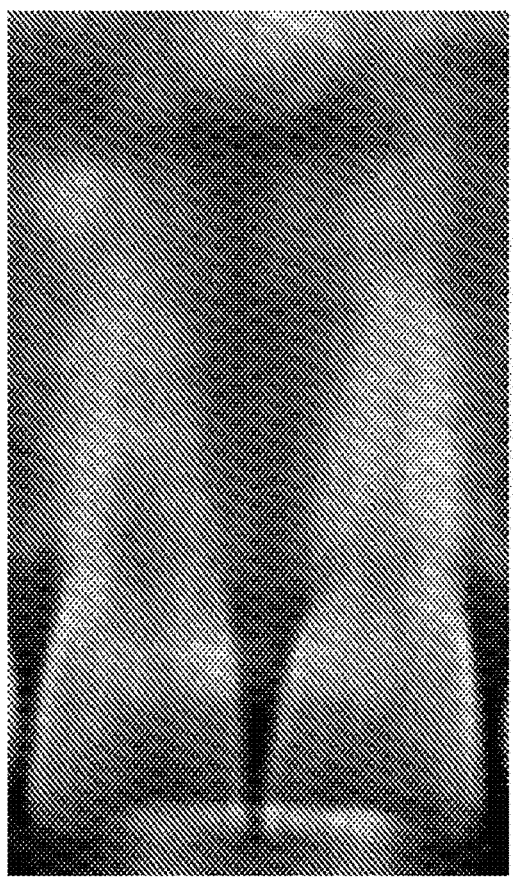
FIG. 7 illustrates schematic diagrams of a fuzzy region before and after a sharpening processing of image according to an embodiment of the present disclosure.
Figure 7:
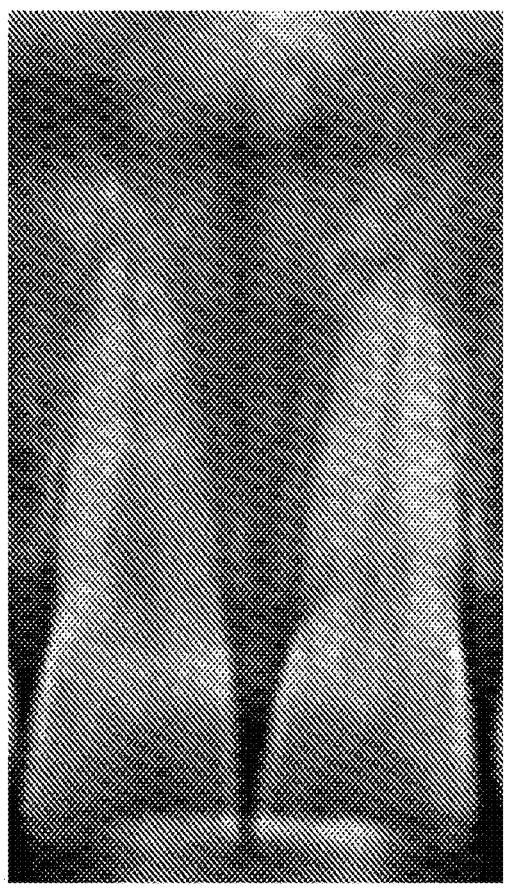

Then, a TDI reorganization is performed on the fuzzy region according to the frames reserved for each row. i.e., the TDI reorganization is performed on the original data after the frame frequency corresponding to each row is changed. Since the frame frequency corresponding to each row is changed, the position of the focusing layer for each row is changed. Finally, the position of the focusing layer as shown in FIG. 3(c) is formed, such that the cusps and the roots of the incisor teeth of which the inclination angle is large may be covered in the focusing layer. It should be understood that, the image becomes clear after the frame frequency is changed, but a size on the left and right direction will become narrow. Linear interpolation may be used to stretch the size of the fuzzy region after the TDI reorganization to an original width. The clear image of the region corresponding to the incisor teeth may be acquired by performing this operation for each row, as shown in FIG. 7. It could be also understood that linear interpolation is a common image processing method for zooming in or zooming out an image (or for stretching the image along a certain direction), which will not described herein.

Figure 8:
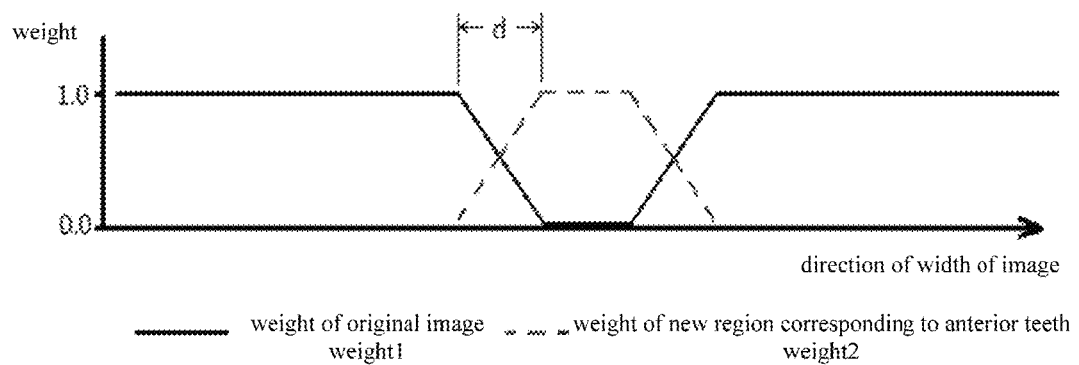
FIG. 8 is a schematic diagram of a corresponding relationship between a first weight and a second weight according to an embodiment of the present disclosure.
Figure 9:
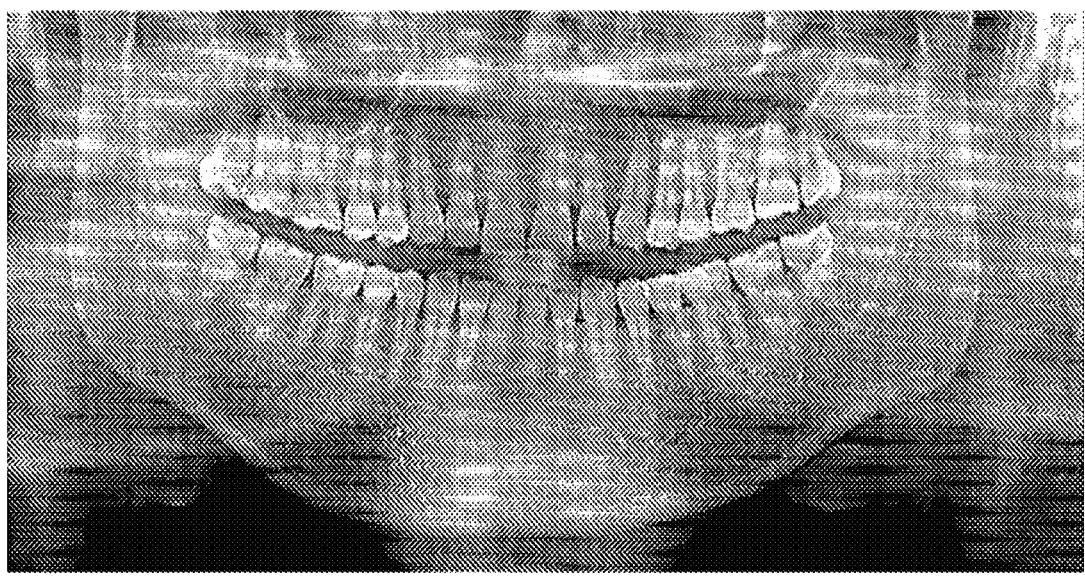
FIG. 9 is a schematic diagram of a displaying effect of a second panoramic image according to an embodiment of the present disclosure.

Then, the region corresponding to the incisor teeth performed the sharpening processing of image is fused with the first panoramic image to generate a second panoramic image, and the fusing process is described as follows. A fusing area of which the width is d may be preset. Weights are set according to a method shown in FIG. 8, so as to acquire a first weight weight1 of the original image (i.e., the first panoramic image) and a second weight weight2 of a new region corresponding to the incisor teeth (i.e., the region of the incisor teeth after the sharpening process of image). A fused image (i.e., the second panoramic image) is acquired by the weight sum method shown in Equation (3). A displaying effect of the second panoramic image is shown in FIG. 9.

$$I_{new} = \text{weight1} * I_0 + \text{weight2} * I_{part\_new} \quad (3)$$

In Equation (3), $I_{new}$ is the fused image, $I_0$ is the original panoramic image before the region corresponding to the incisor teeth is adjusted, $I_{part\_new}$ is clear region corresponding to the incisor teeth adjusted (i.e., right diagram in FIG. 7), weight1 is the weight of the original image, and weight2 is the weight of the new region corresponding to the incisor teeth. In addition, in the embodiments of the present disclosure, a method for setting weight1 and weight2 may be as follows. For a region which is not adjusted, weight2 is set as 0 and weight1 is set as 1. As shown in FIG. 8, a transition region of which the width is d is set between two regions, and weight1 and weight2 in the transition region are set to be linearly distributed from 0 to 1. As closer to the region adjusted, weight1 gets smaller and weight2 gets greater, remaining weight1+weight2==1 all the time.

In conclusion, compared to a traditional method for generating a dental panoramic image, common TDI principle is no longer used for imaging in the present disclosure, instead, different frame frequencies are used for different rows. In other words, imaging in each row is carried out according to the IDE principle, but formation of the whole image is not a whole TDI process, since different frame frequencies are used for different rows. Instead, TDI is performed on many rows separately, in combination with other operations, and finally the fusing is performed to generate the panoramic image. Thus, both the cusps and the roots of teeth of the patient can be covered in the focusing layer by using different frame frequencies for different rows, such that the panoramic image having high resolution can be acquired.

According to the method for generating a dental panoramic image of the embodiments of the present disclosure, the frame frequency of the reference detector may be determined firstly, and the frame frequency of the photographing detector may be determined according to the frame frequency of reference detector; then, teeth of the patient may be photographed according to the frame frequency of the photographing detector to generate the plurality of images; then, the shift and the superposition may be performed on the plurality of images to generate the first panoramic image; then, the fuzzy region in the first panoramic image may be acquired, the frame frequency adjustment may be performed on each row in the fuzzy region to generate the clear image, and the clear image is fused with the first panoramic image to generate the second panoramic image, i.e., the fuzzy region is performed on a sharpening processing by changing the frame frequency thereof, i.e., different changing rules of the frame frequency may be used for imaging for each row of the image, such that both cusps and roots of teeth of the patient may be arranged in a focusing layer, thus generating a clear image and improving definition of the panoramic image.

It should be noted that, in an embodiment of the present disclosure, operations like smoothing, sharpening and contrast adjustment may be performed on the newly generated panoramic image with high resolution according to habits of different user, thus, improving quality of the panoramic image.

Figure 10:
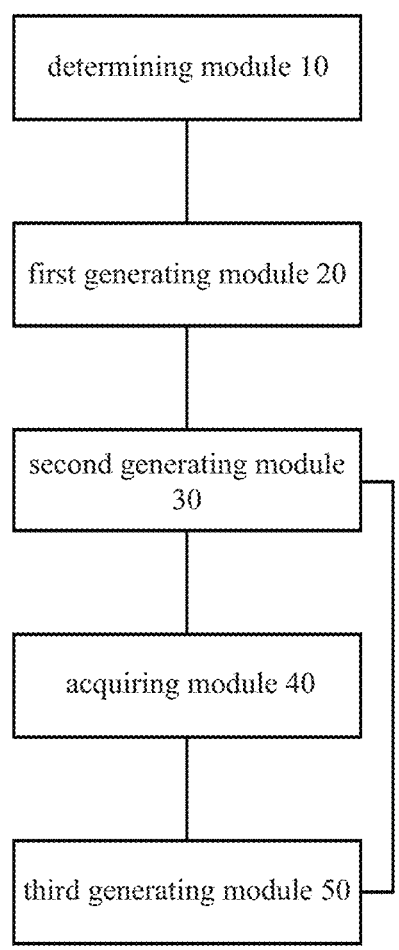
FIG. 10 is a block diagram of an apparatus for generating a dental panoramic image according to an embodiment of the present disclosure.

Corresponding to the method for generating a dental panoramic image provided by the above embodiments, the present disclosure also provides an apparatus for generating a dental panoramic image. Since the apparatus corresponds to the method provided by the above embodiments, implementations of the method are also suitable for the apparatus, which will not be described herein. FIG. 10 is a block diagram of an apparatus for generating a dental panoramic image according to an embodiment of the present disclosure. As shown in FIG. 10, the apparatus includes a determining module 10, a first generating module 20, a second generating module 30, an acquiring module 40 and a third generating module 50.

Specifically, the determining module 10 may be configured to determine a frame frequency of a reference detector, and to determine a frame frequency of a photographing detector according to the frame frequency of the reference detector.

The first generating module 20 may be configured to photograph teeth of a patient according to the frame frequency of the photographing detector to generate a plurality of images.

The second generating module 30 may be configured to perform a shift and superposition on the plurality of images to generate a first panoramic image. Specifically, in the embodiments of the present disclosure, the second generating module 30 may be specifically configured to execute followings. It is assumed that a number of the plurality of images is M, each of the plurality of images has W columns. A counter in is initialized, and let m=1. $m^{th}$ image of the plurality of images is shifted and superposed on $m^{th}$ column to $(m+W-1)^{th}$ column in the first panoramic image. One is added to m and it is judged whether in is smaller than or equal to M. If in is smaller than or equal to M, $m^{th}$ image of the plurality of images is shifted and superposed on $m^{th}$ column to $(m+W-1)^{th}$ column in the first panoramic image until $M^{th}$ image of the plurality of images is shifted and superposed to generate the first panoramic image.

The acquiring module 40 may be configured to acquire a fuzzy region in the first panoramic image.

The third generating module 50 may be configured to perform a frame frequency adjustment on each row in the fuzzy region to generate a clear image, and to fuse the clear image and the first panoramic image to generate a second panoramic image.

Figure 11:
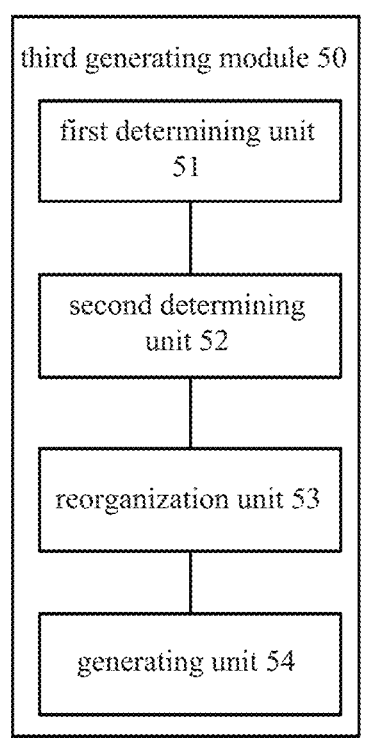
FIG. 11 is a block diagram of a third generating module according to an embodiment of the present disclosure.

Specifically, in an embodiment of the present disclosure, as shown in FIG. 11, the third generating module 50 may include a first determining unit 51, a second determining unit 52, a reorganization unit 53 and a generating unit 54.

Specifically, the first determining unit 51 may be configured to acquire a total number of rows in the fuzzy region, and to determine a frame frequency of the photographing detector corresponding to each row according to a preset frame frequency computation model. The second determining unit 52 may be configured to delete frames in the fuzzy region according to the frame frequency of the photographing detector corresponding to each row and a preset frame extracting model to determine frames reserved for each row. The reorganization unit 53 may be configured to perform a TDI reorganization on the fuzzy region according to the frame reserved for each row to generate the clear image, and to adjust a size of the clear image to be same as a size of the fuzzy region. The generating unit 54 may be configured to fuse the adjusted clear image and the first panoramic image to generate the second panoramic image. In the embodiments of the present disclosure, the preset frame frequency computation model is:

$$F_n(t)=F_0(t)*((k-1)*n+N-k)/(N-1), \quad (1)$$

wherein N is the total number of the rows in the fuzzy region, $F_n(t)$ is a frame frequency of the photographing detector of $n^{th}$ row in the fuzzy region and n=1, 2, ..., N, $F_0(t)$ is the frame frequency of the photographing detector for generating the first panoramic image, k is a frame frequency variation amplitude and 0<k<1.

Additionally, the preset frame extracting model is:

$$l=\text{floor}(p*(F_n(t)/F_0(t)))-\text{floor}((p-1)*(F_n(t)/F_0(t))) \quad (2)$$

wherein floor( ) is an integral function for leaving a fractional part, L is a total number of the frames reserved for the fuzzy region, p=1, 2, ..., L and l<L, $p^{th}$ frame is reserved for using if l is greater than or equal to 1, and $p^{th}$ frame is not reserved for using if is smaller than 1.

Further, in the embodiments of the present disclosure, the generating unit 54 is further configured to determine a first weight of the first panoramic image and a second weight of the adjusted clear image according to a width value of a preset fusing area, and to generate the second panoramic image according to a preset fusing model, the first panoramic image, the first weight, the adjusted clear image and the second weight. In the embodiments of the present disclosure, the preset fusing model is:

$$I_{new}=\text{weight1}*I_0+\text{weight2}*I_{part\_new}, \quad (3)$$

wherein $I_{new}$ a fused image, $I_0$ is the first panoramic image, $I_{part\_new}$ is the adjusted clear image, weight1 is the first weight and weight2 is the second weight.

According to the apparatus for generating a dental panoramic image of the embodiments of the present disclosure, by the determining module, the frame frequency of the reference detector may be determined firstly, and the frame frequency of the photographing detector may be determined according to the frame frequency of the reference detector, teeth of the patient may be photographed by the first generating module according to the frame frequency of the photographing detector to generate the plurality of images, the shift and the superposition may be performed by the second generating module on the plurality of images to generate the first panoramic image, the fuzzy region in the first panoramic image may be acquired by the acquiring module, and the frame frequency adjustment may be performed by the third generating module on each row in the fuzzy region to generate the clear image, and the clear image is fused with the first panoramic image to generate the second panoramic image, i.e., the fuzzy region is performed on a sharpening processing by changing the frame frequency thereof, i.e., different changing rules of the frame frequency may be used for each row of the image, such that both cusps and roots of teeth of the patient may be arranged in a focusing layer, thus generating an clear image, and improving definition of the panoramic image.

In order to achieve the above embodiments, the present disclosure also provides a panoramic camera for photographing teeth, which includes the apparatus for generating a dental panoramic image according to any of the above embodiments of the present disclosure.

It should be understood that, in the embodiments of the present disclosure, the panoramic camera for photographing teeth may be a CT machine with CT functions or a simplex panoramic camera without CT functions, which is not limited in the present disclosure.

According to the panoramic camera of the embodiments of the present disclosure, by the determining module, the frame frequency of the reference detector may be determined firstly, and the frame frequency of the photographing detector may be determined according to the frame frequency of the reference detector, teeth of the patient may be photographed by the first generating module according to the frame frequency of the photographing detector to generate the plurality of images, the shift and the superposition may be performed by the second generating module on the plurality of images to generate the first panoramic image, the fuzzy region in the first panoramic image may be acquired by the acquiring module, and the frame frequency adjustment may be performed by the third generating module on each row in the fuzzy region to generate the clear image, and the clear image is fused with the first panoramic image to generate the second panoramic image, i.e., the fuzzy region is performed on a sharpening processing by changing the frame frequency thereof, i.e., different changing rules of the frame frequency may be used for each row of the image, such that both cusps and roots of teeth of the patient may be arranged in a focusing layer, thus generating an clear image, and improving definition of the panoramic image.

In order to achieve the above embodiments, the present disclosure also provides a storage medium for storing application programs which are configured to execute the method for generating a dental panoramic image according to any of the embodiments of the first aspect of the present disclosure.

In the description of the present disclosure, it should be understood that terms such as "first" and "second" are used herein for purposes of description and are not intended to indicate or imply relative importance or significance. Thus, the feature defined with "first" and "second" may comprise one or more this feature. In the description of the present disclosure, "a plurality of" means at least two, such as two or three, unless specified otherwise.

It will be understood that, the flow chart or any process or method described herein in other manners may represent a module, segment, or portion of code that comprises one or more executable instructions to implement the specified logic function(s) or that comprises one or more executable instructions of the steps of the progress. And the scope of a preferred embodiment of the present disclosure includes other implementations in which the order of execution may differ from that which is depicted in the flow chart, which should be understood by those skilled in the art.

The logic and/or step described in other manners herein or shown in the flow chart, for example, a particular sequence table of executable instructions for realizing the logical function, may be specifically achieved in any computer readable medium to be used by the instruction execution system, device or equipment (such as the system based on computers, the system comprising processors or other systems capable of obtaining the instruction from the instruction execution system, device and equipment and executing the instruction), or to be used in combination with the instruction execution system, device and equipment. As to the specification, "the computer readable medium" may be any device adaptive for including, storing, communicating, propagating or transferring programs to be used by or in combination with the instruction execution system, device or equipment. More specific examples of the computer readable medium comprise but are not limited to: an electronic connection (an electronic device) with one or more wires, a portable computer enclosure (a magnetic device), a random access memory (RAM), a read only memory (ROM), an erasable programmable read-only memory (EPROM or a flash memory), an optical fiber device and a portable compact disk read-only memory (CDROM). In addition, the computer readable medium may even be a paper or other appropriate medium capable of printing programs thereon, this is because, for example, the paper or other appropriate medium may be optically scanned and then edited, decrypted or processed with other appropriate methods when necessary to obtain the programs in an electric manner, and then the programs may be stored in the computer memories.

It should be understood that each part of the present disclosure may be realized by the hardware, software, firmware or their combination. In the above embodiments, a plurality of steps or methods may be realized by the software or firmware stored in the memory and executed by the appropriate instruction execution system. For example, if it is realized by the hardware, likewise in another embodiment, the steps or methods may be realized by one or a combination of the following techniques known in the art: a discrete logic circuit having a logic gate circuit for realizing a logic function of a data signal, an application-specific integrated circuit having an appropriate combination logic gate circuit, a programmable gate array (PGA), a field programmable gate array (FPGA), etc.

Those skilled in the art shall understand that all or parts of the steps in the above exemplifying method of the present disclosure may be achieved by commanding the related hardware with programs. The programs may be stored in a computer readable storage medium, and the programs comprise one or a combination of the steps in the method embodiments of the present disclosure when run on a computer.

In addition, each function cell of the embodiments of the present disclosure may be integrated in a processing module, or these cells may be separate physical existence, or two or more cells are integrated in a processing module. The integrated module may be realized in a form of hardware or in a form of software function modules. When the integrated module is realized in a form of software function module and is sold or used as a standalone product, the integrated module nay be stored in a computer readable storage medium.

The storage medium mentioned above may be read-only memories, magnetic disks, CD, etc.

Reference throughout this specification to "one embodiment", "some embodiments," "an embodiment" "a specific example," or "some examples," means that a particular feature, structure, material, or characteristic described in connection with the embodiment or example is included in at least one embodiment or example of the present disclosure. Thus, the appearances of the phrases in various places throughout this specification are not necessarily referring to the same embodiment or example of the present disclosure. Furthermore, the particular features, structures, materials, or characteristics may be combined in any suitable manner in one or more embodiments or examples. In addition, in a case without contradictions, different embodiments or examples or features of different embodiments or examples may be combined by those skilled in the art.

Although explanatory embodiments have been shown and described, it would be appreciated that the above embodiments are explanatory and cannot be construed to limit the present disclosure, and changes, alternatives, and modifications can be made in the embodiments without departing from scope of the present disclosure by those skilled in the art.

What is claimed is:

1. A method for generating a dental panoramic image, comprising:
   determining a frame frequency of a reference detector, and determining a frame frequency of a photographing detector according to the frame frequency of the reference detector;
   processing a photograph of teeth of a patient according to the frame frequency of the photographing detector to generate a plurality of images;
   performing a shift and a superposition on the plurality of images to generate a first panoramic image;
   acquiring a fuzzy region in the first panoramic image; and
   performing a frame frequency adjustment on each row in the fuzzy region to generate a clear image, and fusing the clear image and the first panoramic image to generate a second panoramic image.

2. The method according to claim 1, wherein performing a shift and a superposition on the plurality of images to generate a first panoramic image comprises:
   shifting and superposing $m^{th}$ image of the plurality of images on $m^{th}$ column to $(m+W-1)^{th}$ column in the first panoramic image, wherein, m is a positive integer and $1 < m < M$,
   M is a number of the plurality of images, and W is a number of columns of each of the plurality of images.

3. The method according to claim 1, wherein performing a frame frequency adjustment on each row in the fuzzy region to generate a clear image, and fusing the clear image and the first panoramic image to generate a second panoramic image comprises:
  acquiring a total number of rows in the fuzzy region, and determining a frame frequency of the photographing detector corresponding to each row;
  deleting frames in the fuzzy region according to the frame frequency of the photographing detector corresponding to each row and a preset frame extracting model to determine frames reserved for each row;
  performing a time delay integration TDI reorganization on the fuzzy region according to the frames reserved for each row to generate the clear image, and adjusting a size of the clear image to be same as a size of the fuzzy region; and
  fusing the adjusted clear image and the first panoramic image to generate the second panoramic image.

4. The method according to claim 3, wherein the preset frame frequency computation model is:

$$F_n(t)=F_0(t)*((k-1)*n+N-k)/(N-1),$$

where, N is the total number of the rows in the fuzzy region, $F_n(t)$ is a frame frequency of the photographing detector of $n^{th}$ row in the fuzzy region and n=1, 2, ..., N, $F_0(t)$ is the frame frequency of the photographing detector for generating the first panoramic image, and k is a frame frequency variation amplitude and 0<k<1.

5. The method according to claim 3, wherein the preset frame extracting model is:

$$l = \text{floor}\left(p*\left(\frac{F_n(t)}{F_0(t)}\right)\right) - \text{floor}\left((p-1)*\left(\frac{F_n(t)}{F_0(t)}\right)\right),$$

where, floor( ) is an integral function for leaving a fractional part, L is a total number of the frames reserved for the fuzzy region, p=1, 2, ..., L and l<L, $p^{th}$ frame is reserved for using if l is greater than or equal to 1, and $p^{th}$ frame is not reserved for using if l is smaller than 1.

6. The method according to claim 1, wherein fusing the adjusted clear image and the first panoramic image to generate the second panoramic image comprises:
  determining a first weight of the first panoramic image and a second weight of the adjusted clear image according to a width value of a preset fusing area; and
  generating the second panoramic image according to a preset fusing model, the first panoramic image, the first weight, the adjusted clear image, and the second weight.

7. The method according to claim 6, wherein the preset fusing model is:

$$I_{new}=\text{weight1}*I_0+\text{weight2}*I_{part\_new},$$

where, $I_{new}$ is the second panoramic image, $I_0$ is the first panoramic image, $I_{part\_new}$ is the adjusted clear image, weight1 is the first weight, and weight2 is the second weight.

8. An apparatus for generating a dental panoramic image, comprising:
  a processor;
  memory for storing instructions executable by the processor;
  wherein the processor is configured to:
    determine a frame frequency of a reference detector, and determine a frame frequency of a photographing detector according to the frame frequency of the reference detector;
    process a photograph of teeth of a patient according to the frame frequency of the photographing detector to generate a plurality of images;
    perform a shift and a superposition on the plurality of images to generate a first panoramic image;
    acquire a fuzzy region in the first panoramic image; and
    perform a frame frequency adjustment on each row in the fuzzy region to generate a clear image, and fuse the clear image and the first panoramic image to generate a second panoramic image.

9. The apparatus according to claim 8, wherein the processor is further configured to:
  shift and superpose $m^{th}$ image of the plurality of images on $m^{th}$ column to $(m+W-1)^{th}$ column in the first panoramic image, wherein, m is a positive integer and 1<m<M, M is a number of the plurality of images, and W is a number of columns of each of the plurality of images.

10. The apparatus according to claim 8, wherein the processor is further configured to:
  acquire a total number of rows in the fuzzy region, and determine a frame frequency of the photographing detector corresponding to each row;
  delete frames in the fuzzy region according to the frame frequency of the photographing detector corresponding to each row and a preset frame extracting model to determine frames reserved for each row;
  perform a time delay integration TDI reorganization on the fuzzy region according to the frame reserved for each row to generate the clear image, and adjust a size of the clear image to be same as a size of the fuzzy region; and
  fuse the adjusted clear image and the first panoramic image to generate the second panoramic image.

11. The apparatus according to claim 10, wherein the preset frame frequency computation model is:

$$F_n(t)=F_0(t)*((k-1)*n+N-k)/(N-1),$$

where, N is the total number of the rows in the fuzzy region, $F_n(t)$ is a frame frequency of the photographing detector of $n^{th}$ row in the fuzzy region and n=1, 2, ..., N, $F_0(t)$ is the frame frequency of the photographing detector for generating the first panoramic image, and k is a frame frequency variation amplitude and 0<k<1.

12. The apparatus according to claim 10, wherein the preset frame extracting model is:

$$l = \text{floor}\left(p*\left(\frac{F_n(t)}{F_0(t)}\right)\right) - \text{floor}\left((p-1)*\left(\frac{F_n(t)}{F_0(t)}\right)\right),$$

where, floor( ) is an integral function for leaving a fractional part, L is a total number of the frames reserved for the fuzzy region, p=1, 2, ..., L and l<L, $p^{th}$ frame is reserved for using if l is greater than or equal to 1, and $p^{th}$ frame is not reserved for using if l is smaller than 1.

13. The apparatus according to claim 8, wherein the processor is further configured to:
  determine a first weight of the first panoramic image and a second weight of the adjusted clear image according to a width value of a preset fusing area; and generate the second panoramic image according to a preset fusing model, the first panoramic image, the first weight, the adjusted clear image, and the second weight.

14. The apparatus according to claim 13, wherein the preset fusing model is:

$$I_{new}=\text{weight1}*I_0+\text{weight2}*I_{part\_new}$$

where, $I_{new}$ is the second panoramic image, $I_0$ is the first panoramic image, $I_{part\_new}$ is the adjusted clear image, weight1 is the first weight, and weight2 is the second weight.

15. A panoramic camera for photographing teeth, comprising an apparatus for generating a dental panoramic image, wherein the apparatus comprises:
a processor;
memory for storing instructions executable by the processor;
wherein the processor is configured to:
determine a frame frequency of a reference detector, and determine a frame frequency of a photographing detector according to the frame frequency of the reference detector;
process a photograph of teeth of a patient according to the frame frequency of the photographing detector to generate a plurality of images;
perform a shift and a superposition on the plurality of images to generate a first panoramic image;
acquire a fuzzy region in the first panoramic image; and
perform a frame frequency adjustment on each row in the fuzzy region to generate a clear image, and fuse the clear image and the first panoramic image to generate a second panoramic image.

16. The panoramic camera according to claim 15, wherein the processor is further configured to:
shift and superpose $m^{th}$ image of the plurality of images on $m^{th}$ column to $(m+W-1)^{th}$ column in the first panoramic image, wherein, m is a positive integer and 1<m≤M, <M, M is a number of the plurality of images, and W is a number of columns of each of the plurality of images.

17. The panoramic camera according to claim 15, wherein the processor is further configured to:
acquire a total number of rows in the fuzzy region, and determine a frame frequency of the photographing detector corresponding to each row;
delete frames in the fuzzy region according to the frame frequency of the photographing detector corresponding to each row and a preset frame extracting model to determine frames reserved for each row;
perform a time delay integration TDI reorganization on the fuzzy region according to the frame reserved for each row to generate the clear image, and adjust a size of the clear image to be same as a size of the fuzzy region; and
fuse the adjusted clear image and the first panoramic image to generate the second panoramic image.

18. The panoramic camera according to claim 17, wherein the preset frame frequency computation model is:

$$F_n(t)=F_0(t)*((k-1)*n+N-k)/(N-1),$$

where, N is the total number of the rows in the fuzzy region, $F_n(t)$ is a frame frequency of the photographing detector of $n^{th}$ row in the fuzzy region and n=1, 2, ..., N, $F_0(t)$ is the frame frequency of the photographing detector for generating the first panoramic image, and k is a frame frequency variation amplitude and 0<k<1; and the preset frame extracting model is:

$$l=\text{floor}\left(p*\left(\frac{F_n(t)}{F_0(t)}\right)\right)-\text{floor}\left((p-1)*\left(\frac{F_n(t)}{F_0(t)}\right)\right),$$

where, floor( ) is an integral function for leaving a fractional part, L is a total number of the frames reserved for the fuzzy region, p=1, 2, ..., L and l<L, $p^{th}$ frame is reserved for using if l is greater than or equal to 1, and $p^{th}$ frame is not reserved for using if l is smaller than 1.

19. The panoramic camera according to claim 15, wherein the processor is further configured to:
determine a first weight of the first panoramic image and a second weight of the adjusted clear image according to a width value of a preset fusing area; and
generate the second panoramic image according to a preset fusing model, the first panoramic image, the first weight, the adjusted clear image and the second weight;
where the preset fusing model is:

$$I_{new}=\text{weight1}*I_0+\text{weight2}*I_{part\_new},$$

where, $I_{new}$ is the second panoramic image, $I_0$ is the first panoramic image, $I_{part\_new}$ is the adjusted clear image, weight1 is the first weight and weight2 is the second weight.

* * * * *